(12) United States Patent
Shuros et al.

(10) Patent No.: US 8,406,879 B2
(45) Date of Patent: Mar. 26, 2013

(54) RATE ADAPTIVE CARDIAC PACING SYSTEMS AND METHODS

(75) Inventors: Allan C. Shuros, St. Paul, MN (US); Donald L. Hopper, Maple Grove, MN (US); Michael J. Kane, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 213 days.

(21) Appl. No.: 11/613,740

(22) Filed: Dec. 20, 2006

(65) Prior Publication Data

US 2008/0154139 A1    Jun. 26, 2008

(51) Int. Cl.
*A61N 1/00* (2006.01)
(52) U.S. Cl. ............................. 607/28; 607/13; 607/17
(58) Field of Classification Search ............... 607/13, 607/28
See application file for complete search history.

(56) References Cited

U.S. PATENT DOCUMENTS

| | | | |
|---|---|---|---|
| 4,535,774 A | | 8/1985 | Olson |
| 4,585,006 A * | | 4/1986 | Livingston et al. ............ 607/10 |
| 4,686,987 A | | 8/1987 | Salo et al. |
| 4,766,901 A * | | 8/1988 | Callaghan ...................... 607/26 |
| 4,802,481 A | | 2/1989 | Schroeppel |
| 4,884,576 A * | | 12/1989 | Alt ................................... 607/18 |
| 4,936,304 A | | 6/1990 | Kresh et al. |
| 5,044,366 A | | 9/1991 | Alt |
| 5,154,171 A | | 10/1992 | Chirife |
| 5,156,147 A | | 10/1992 | Warren et al. |
| 5,188,106 A * | | 2/1993 | Nappholz et al. ............... 607/24 |
| 5,391,190 A | | 2/1995 | Pederson et al. |
| 5,423,870 A | | 6/1995 | Olive et al. |
| 5,697,957 A * | | 12/1997 | Noren et al. .................... 607/28 |
| 5,741,310 A * | | 4/1998 | Wittkampf ...................... 607/14 |
| 5,935,081 A | | 8/1999 | Kadhiresan |
| 6,016,446 A * | | 1/2000 | Belalcazar ...................... 607/13 |
| H1929 H * | | 12/2000 | Citak .............................. 607/28 |
| 6,298,269 B1 * | | 10/2001 | Sweeney ......................... 607/28 |
| 6,353,761 B1 * | | 3/2002 | Conley et al. ................... 607/28 |

(Continued)

FOREIGN PATENT DOCUMENTS

| DE | 198 36 496 | 2/2000 |
|---|---|---|
| JP | 7088199 | 11/1996 |

(Continued)

OTHER PUBLICATIONS

"Hemodynamics in Critical Care Hemodynamic Monitoring Overview", *Nursebob's MICU/CCU Survival Guide (section 5)* www.nursebob.com Dec. 4, 2000 , 1-9.

(Continued)

*Primary Examiner* — Nicole F Lavert
(74) *Attorney, Agent, or Firm* — Pauly, DeVries Smith & Deffner, L.L.C.

(57) ABSTRACT

The invention relates to cardiac rhythm management systems, and more particularly, to rate adaptive cardiac pacing systems and methods. In an embodiment, the invention includes a method for providing rate-adaptive cardiac pacing therapy from an implantable medical device, the method including sensing a pulmonary function of a patient; determining a rate of change in the pulmonary function; sensing a cardiac function of the patient; determining a rate of change in the cardiac function; and calculating a target pacing rate based on an existing pacing rate, the rate of change in the pulmonary function, and the rate of change in the cardiac function.

14 Claims, 8 Drawing Sheets

U.S. PATENT DOCUMENTS

| | | | |
|---|---|---|---|
| 6,363,281 B1 * | 3/2002 | Zhu et al. | 607/28 |
| 6,411,850 B1 | 6/2002 | Kay et al. | |
| 6,418,343 B1 * | 7/2002 | Zhang et al. | 607/9 |
| 6,463,326 B1 * | 10/2002 | Hartley et al. | 607/20 |
| 6,473,649 B1 * | 10/2002 | Gryzwa et al. | 607/28 |
| 6,477,420 B1 * | 11/2002 | Struble et al. | 607/14 |
| 6,564,100 B2 * | 5/2003 | Warren et al. | 607/28 |
| 6,587,723 B1 * | 7/2003 | Sloman et al. | 607/28 |
| 6,671,551 B2 * | 12/2003 | Conley et al. | 607/28 |
| 6,772,009 B2 * | 8/2004 | Zhang et al. | 607/9 |
| 6,928,325 B2 | 8/2005 | Zhu et al. | |
| 6,975,903 B1 * | 12/2005 | Min et al. | 607/24 |
| 7,062,326 B2 * | 6/2006 | Huvelle et al. | 607/18 |
| 7,096,065 B2 * | 8/2006 | Conley et al. | 607/27 |
| 7,328,067 B2 * | 2/2008 | Zhu et al. | 607/28 |
| 2003/0204211 A1 | 10/2003 | Condie et al. | |
| 2004/0015195 A1 | 1/2004 | Daum et al. | |
| 2004/0220642 A1 * | 11/2004 | Zhu et al. | 607/28 |
| 2004/0230244 A1 * | 11/2004 | Conley et al. | 607/28 |
| 2005/0004613 A1 * | 1/2005 | Zhang et al. | 607/28 |
| 2005/0096720 A1 * | 5/2005 | Sharma et al. | 607/122 |
| 2005/0137630 A1 * | 6/2005 | Ding et al. | 607/9 |
| 2005/0251215 A1 * | 11/2005 | Dujmovic et al. | 607/8 |
| 2005/0267541 A1 | 12/2005 | Scheiner et al. | |
| 2006/0036290 A1 * | 2/2006 | Hopper et al. | 607/17 |
| 2006/0129198 A1 * | 6/2006 | Zhang | 607/28 |
| 2006/0212084 A1 * | 9/2006 | Yost et al. | 607/28 |
| 2006/0235480 A1 * | 10/2006 | Schecter | 607/18 |
| 2006/0253174 A1 * | 11/2006 | King | 607/62 |
| 2006/0265019 A1 | 11/2006 | Sun et al. | |
| 2006/0287681 A1 * | 12/2006 | Yonce et al. | 607/5 |
| 2007/0005114 A1 * | 1/2007 | Salo et al. | 607/17 |
| 2008/0021507 A1 * | 1/2008 | Libbus et al. | 607/17 |
| 2008/0027495 A1 * | 1/2008 | Prinzen et al. | 607/9 |
| 2010/0045612 A1 | 2/2010 | Molne | |

FOREIGN PATENT DOCUMENTS

| | | |
|---|---|---|
| JP | 63177872 | 6/1998 |
| WO | WO-00/09012 | 2/2000 |

OTHER PUBLICATIONS

Abi-Samra, Freddy M. et al., "Pacing Techniques in Heart Failure: Current Concepts and Future Outlook", *Congestive Heart Failure* www.medscape.com 2003, 9(4):214-223,229.

Barold, Serge S. et al., "Contemprary Issues in Rate-Adaptive Pacing", *Clinical Cardiology* www.clinicalcardiology.org Apr. 24, 1997, 1-7.

Clark, J. M. et al., "Breathing Patterns During Submaximal and Maximal Exercise in Elite Oarsmen", *the American Physiological Society* 1983, 440-446.

Clementy, J et al., "Validation by serial standardized testing of a new rate-responsive pacemaker sensor baded on variations in myocardial contractility", *Europace* vol. 3 www.idealibrary.com Apr. 2003, 124-131.

Dell'Orto, Simonetta et al., "Sensors for Rate Responsive Pacing", *Indian Pacing and Electrophysiology Journal* (Issn, 0972-6292) 4(3) www.ipej.org 2004, 137-145.

Kink, A. et al., "Impedance Controlled Pacing Rate Limits in Cardiac Pacemakers—Experimental Validation on Isolated Heart", *International Journal of Bioelectromagnetism* vol. 5, No. 1 www.ijbem.org Aug. 26, 2003, 63-64.

LaFortuna, Claudio L. et al., "Inspiratory Flow Pattern in Humans", *the American Physiological Society* 1984, 1111-1119.

McParland, Colm et al., "Effect of Physical Training on Breathing Pattern During Progressive Exercise", *Resperation Physiology* 1992, 90:311-323.

Min, Mart et al., "Abstract: Thoracic bioimpedance as a basis for pacing control", *Ann. N Y Acad Sci.* (ISSN: 0077-8923) www.medscape.com 1999, 873:155-166.

Rowland, Thomas et al., "Cardiovascular Responses to Exercise in Childres and Adolescents With Myocardial Dysfunction", *American Heart Journal* www.medscape.com 1999, 137(1):126-133.

Syabbalo, N. C. et al., "Differential Ventilatory Control During Constant Work Rate and Incremental Exercise", *Respiration Physiology* 1994, 97:175-187.

Tse, Hung-Fat et al., "The Incremental Benefit of Rate-Adaptive Pacin on Exercise Performance During Cardiac Resynchronization Therapy", *J.A.C.C.* 2005, 46(12):2292-2297.

International Search Report mailed Jul. 4, 2008, in foreign counterpart application PCT/US2007/08804.

"Japanese Office Action Received", for Japanese Application No. 2009-543162, corresponding to U.S. Appl. No. 11/613,740, mailed Nov. 17, 2011, (pp. 31) Including English translation.

Japanese Office Action Received, for Japanese Application No. 2009-543162, corresponding to U.S. Appl. No. 11/613,740, mailed Jul. 5, 2012, including English translation.

\* cited by examiner

RATE ADAPTIVE CARDIAC PACING SYSTEMS AND METHODS

FIELD OF THE INVENTION

The invention relates to cardiac rhythm management systems, and more particularly, to rate adaptive cardiac pacing systems and methods.

BACKGROUND OF THE INVENTION

Implantable medical devices can be used to provide pacing therapy to patients who have cardiac rhythm problems. For example, an implanted medical device may provide pacing therapy to a patient with sinus node dysfunction, where the heart fails to properly initiate depolarization waves, or an atrio-ventricular conduction disturbance, where the conduction of depolarization waves through the heart tissue is impaired. Implantable medical devices with pacing functionality can include pacemakers, cardiac resynchronization therapy (CRT) devices, remodeling control therapy (RCT) devices, and implantable cardioverter defibrillators (ICD).

Implanted medical devices with pacing functionality, such as a pacemaker, typically deliver a pacing pulse of electricity to the heart in order to produce a heartbeat at the correct time. The implanted medical device includes electronic circuitry that is contained within an enclosure, often called a can. The can and associated electronics are implanted in the patient's chest and one or more leads are routed from the can, through the patient's vasculature, and to the patient's heart tissue. Electrical pulses are delivered through the leads to the heart tissue, initiating contraction of the heart.

One issue associated with cardiac pacing therapy is the need to adapt the pacing rate in response to the changing metabolic demands of the patient. For example, while a patient is sitting, sleeping, or otherwise being sedentary, the patient's cardiac output requirements are relatively low. However, when engaged in physical activity, a patient's cardiac output requirements increase in order to transport more oxygen to, and carbon dioxide from, various body tissues. The greater the intensity of the physical activity, the greater the cardiac output required to sustain the activity.

Strategies have been devised for adapting the pacing of the heart in response to exercise or exertion, referred to as "adaptive rate pacing" or "rate adaptive pacing". These strategies generally depend on measuring a parameter that serves as an index of exertion and then adjusting the pacing rate in response to changes in the measured parameter. However, these strategies frequently modulate the pacing rate inappropriately because the parameters used do not always correlate well with exertion. For example, in the case of accelerometer data, it is difficult for the device to determine whether the body motion sensed is the result of the patient's exertion or whether it is attributable to other conditions such as riding in a car on a bumpy road or in an airplane that is accelerating rapidly.

With many known rate adaptive pacing strategies, it is necessary to apply a pacing gain rate, that is, the rate at which the pacing rate increases as a function of exertion, and it is also necessary to set a maximum pacing rate. Values for the pacing gain rate and maximum pacing rate are generally determined based on statistical averages derived from physiological studies. Frequently, these statistical average values are used across all patients. However, even among individuals of the same age group, there can be a wide variation in physiology that is related to the degree and scope of cardiac disease and other individual differences. Thus, where a statistical average physiological characteristic is used, it will not be ideal for all patients, and in fact may be significantly inappropriate for some patients. For at least these reasons, a need exists for improved rate adaptive cardiac pacing systems and methods.

SUMMARY OF THE INVENTION

The invention relates to rate adaptive cardiac pacing systems and methods. In one embodiment, the invention relates to a method for providing rate-adaptive cardiac pacing therapy from an implantable medical device. The method includes sensing a pulmonary function of a patient and determining a rate of change in the pulmonary function. The method further includes sensing a cardiac function of the patient and determining a rate of change in the cardiac function. The method also includes calculating a target pacing rate based on an existing pacing rate, the rate of change in the pulmonary function, and the rate of change in the cardiac function.

In a second embodiment, the invention relates to a method for controlling a cardiac rhythm management device in response to exertion of a patient. The method includes sensing the patient's pulmonary function at a first time $t_1$ and at a second time $t_2$, and then calculating a rate of change of the pulmonary function between time $t_1$ and time $t_2$. The method further includes sensing the patient's cardiac function at time $t_3$ and at time $t_4$, and calculating a rate of change of the cardiac function between time $t_3$ and time $t_4$. The method also includes setting a desired pacing rate by increasing an existing pacing rate proportionately to the rate of change of the pulmonary function when the rate of change of the pulmonary function is positive and the rate of change of cardiac function is not negative.

A third embodiment of the invention relates to a method for providing cardiac pacing therapy to a patient. The method includes sensing a pulmonary function and a cardiac function of the patient, calculating a cardiac pacing rate based on the pulmonary function, and calculating a cardiac pacing upper limit based on the cardiac function. The method further includes providing cardiac pacing at the calculated cardiac pacing rate so long as the calculated cardiac pacing rate is equal to or less than the cardiac pacing upper limit.

A fourth embodiment of the invention relates to a cardiac rhythm management device. The device includes a pulse generator for generating electrical pulses to be delivered to a heart at a pacing rate, a processor in communication with the pulse generator, and one or more sensors for sensing pulmonary function and cardiac function, where the one or more sensors are in communication with the processor. The processor of the device is configured to increase the pacing rate if the pulmonary function is increasing with time and the cardiac function is not decreasing with time, to maintain the pacing rate if the pulmonary function is increasing with time and the cardiac function is decreasing with time, and decrease the pacing rate if the pulmonary function is decreasing with time.

A fifth embodiment of the invention relates to a method for adjusting an AV (atrio-ventricular) delay during dual-chamber rate-adaptive cardiac pacing therapy. The method includes monitoring a cardiac function of a patient, where the cardiac function correlates to either stroke volume or cardiac contractility. The method further includes determining a rate of change in the cardiac function, and calculating a target AV delay based on an existing AV delay and the rate of change in the cardiac function.

Further embodiments are also described herein. The invention may be more completely understood by considering the detailed description of various embodiments of the invention that follows in connection with the accompanying drawings.

BRIEF DESCRIPTION OF THE DRAWINGS

The invention may be more completely understood in connection with the following drawings, in which.

DETAILED DESCRIPTION OF THE INVENTION

Figure 1:
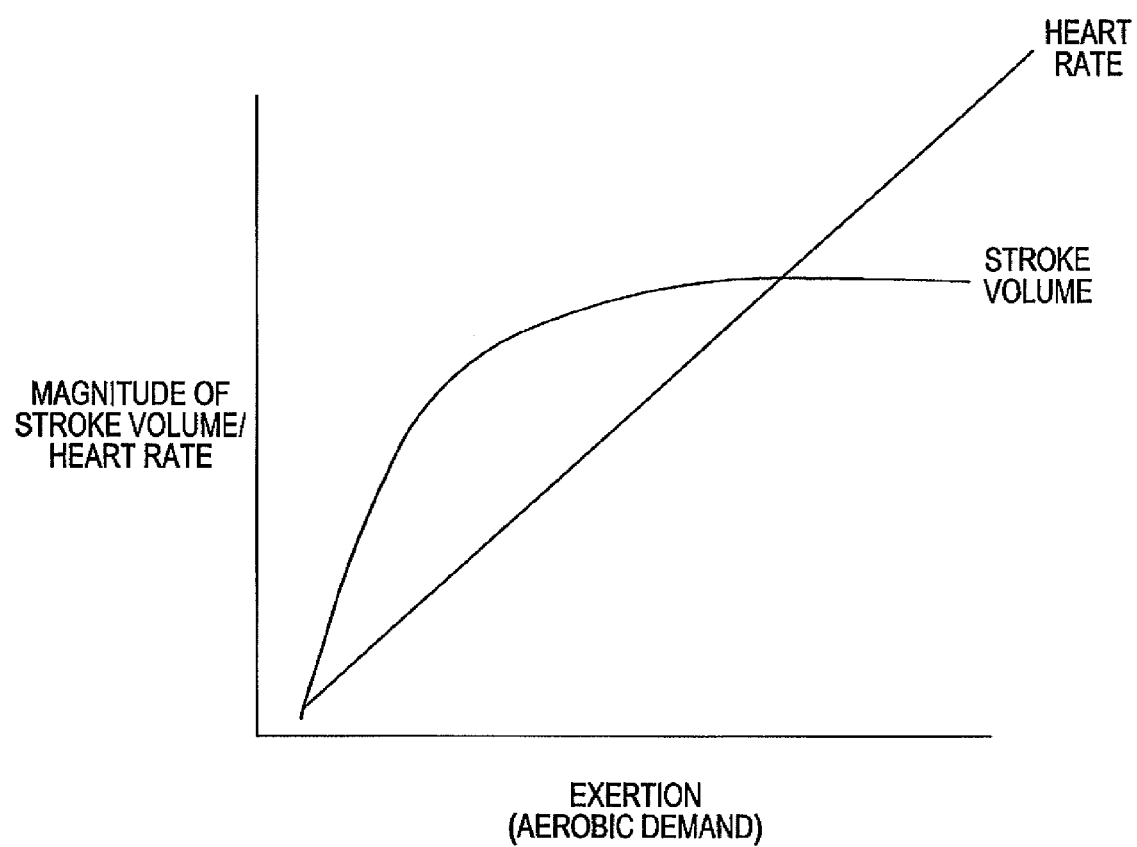
FIG. 1 is a chart showing heart rate and stroke volume as a function of aerobic demand in a typical healthy person.

In the heart of a healthy person, cardiac output is naturally increased in response to exertion in order to deliver increased blood flow to satisfy physiological demands. Cardiac output refers to the volumetric blood flow being pumped by the heart, and is defined as the product of stroke volume and heart rate. Stroke volume is the volume of blood that is ejected from the ventricle (right or left) during each contraction of the heart. A normal, healthy person's body increases both stroke volume and heart rate as necessary to satisfy the body's requirement for cardiac output. The characteristic increases of stroke volume and heart rate in response to exertion in a healthy heart are shown in FIG. 1. As exertion increases from a starting level, stroke volume typically increases rapidly and then gradually plateaus. Stroke volume is increased through a number of mechanisms, including increased ventricular preload (the volume of blood present in a ventricle of the heart, after passive filling and atrial contraction), decreased ventricular afterload (the resistance to the flow of blood out of the heart), and increased myocardial contractility. In contrast to stroke volume, heart rate increases roughly linearly with exertion in a healthy patient. As such, after stroke volume has plateaued at high levels of exertion, additional cardiac output is achieved though further increases in heart rate and not stroke volume.

Some cardiac pacing devices can increase heart rate in order to respond to physiological requirements for increased cardiac output. The adaptation of pacing rate based on physiological demand can be referred to as "rate adaptive pacing" or "adaptive rate pacing." However, one issue associated with implementing rate adaptive pacing is that the appropriate gain rate (that is, the slope of the pacing rate charted against exertion or metabolic demand) and the suitable maximum heart rate can vary for each person. Therefore, a gain rate that is appropriate for one patient may not be appropriate for another patient. As a further complication, the appropriate gain rate and maximum heart rate for a particular individual are actually dynamic variables that can vary with time as their disease progresses and/or as their physiology changes. Rate adaptive pacing can be applied in the context of pacing therapy for various groups of patients. By way of example, rate adaptive pacing can be applied in pacing therapy for patients who are chronotropically incompetent.

Figure 2:
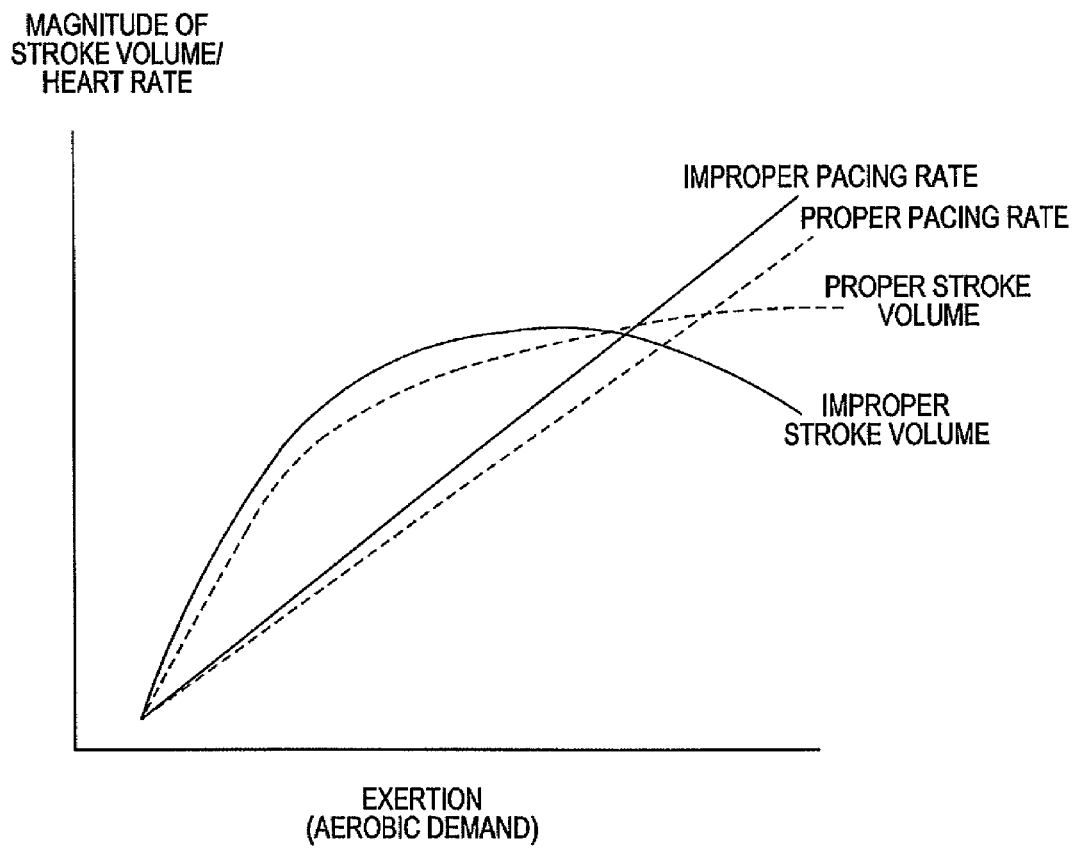
FIG. 2 is a chart showing heart rate and stroke volume as a function of aerobic demand showing the effects of an improper pacing rate.

Providing pacing therapy at an inappropriately fast rate can lead to a reduction in stroke volume. FIG. 2 illustrates the effects of a pacing rate that is too fast for a particular patient. The dashed lines show an ideal pacing rate and a corresponding stroke volume plot. In contrast, the solid lines show a pacing rate that increases too quickly, causing the stroke volume to transition to a negative (i.e., decreasing) slope at a certain point. The negative slope of the stroke volume plot indicates that further increases in heart rate are resulting in lower volume of blood pumped per stroke. One reason for this effect is that the amount of blood pumped by the ventricle with each contraction is limited by the amount of blood passing into the ventricle from the corresponding atrium during the interval of time in between each ventricular contraction. In a situation where the heart is being paced too fast, the interval between ventricular contractions is too short to allow optimal filling of the ventricle.

A reduction in stroke volume (e.g., a negative stroke volume slope) reflects inefficient functioning of the heart and can lead to potentially dangerous side effects. When the slope of the stroke volume plot becomes negative, the heart is operating inefficiently because each contraction of the heart is pumping less blood per stroke than it could at a slower pacing rate. The total energy consumed by the heart is believed to be largely a function of heart rate, so that when the stroke volume slope becomes negative, the energy expended by the cardiac muscle per unit volume of blood pumped increases. The higher the heart rate, the more energy expended by the cardiac muscle per unit of time. The larger the energy requirements of the cardiac muscle, the more blood must flow to the cardiac muscle to meet demand. However, if the stroke volume slope is negative then cardiac output may not be increasing sufficiently to meet the increased demand of the cardiac tissue. Therefore, inefficient functioning of the heart creates a risk of ischemia or even myocardial infarction (i.e., a heart attack), particularly in patients who already have some degree of cardiac disease.

For at least these reasons, it is desirable for a pacemaker or other medical device to provide a pacing rate that is appropriate for each individual patient, and in particular, to provide a pacing rate that is not inappropriately fast such that the stroke volume plot becomes negative. The present invention includes systems and methods for providing adaptive rate pacing that is not inappropriately fast. The present invention also includes systems and methods for providing adaptive rate pacing that prevent inefficient functioning of the heart. In some embodiments, the adaptive rate pacing system and/or method of the invention can include a measurement of pulmonary function in order to establish the level of exertion of the patient and a measurement of cardiac function in order to modulate the pacing rate. For example, embodiments can include a pacemaker or other device configured to implement a rate adaptive pacing method that includes a measurement of pulmonary function in order to establish the level of exertion of the patient and a measurement of cardiac function in order to modulate the pacing rate.

In some embodiments, the rate of change of the pulmonary function and the rate of change of the cardiac function are sensed. Based on the rate of change of the pulmonary function and the cardiac function, a target pacing rate is determined. In some embodiments, if the cardiac function is decreasing, diminished cardiac stroke volume is indicated and the target pacing rate is not increased above an existing pacing rate. If the pulmonary function is increasing and the cardiac function is increasing, increasing metabolic need and suitable cardiac performance is indicated, and the target pacing rate is increased. If the pulmonary function is decreasing, decreasing metabolic need is indicated and the target pacing rate is decreased. Other embodiments are also included herein.

Figure 3:
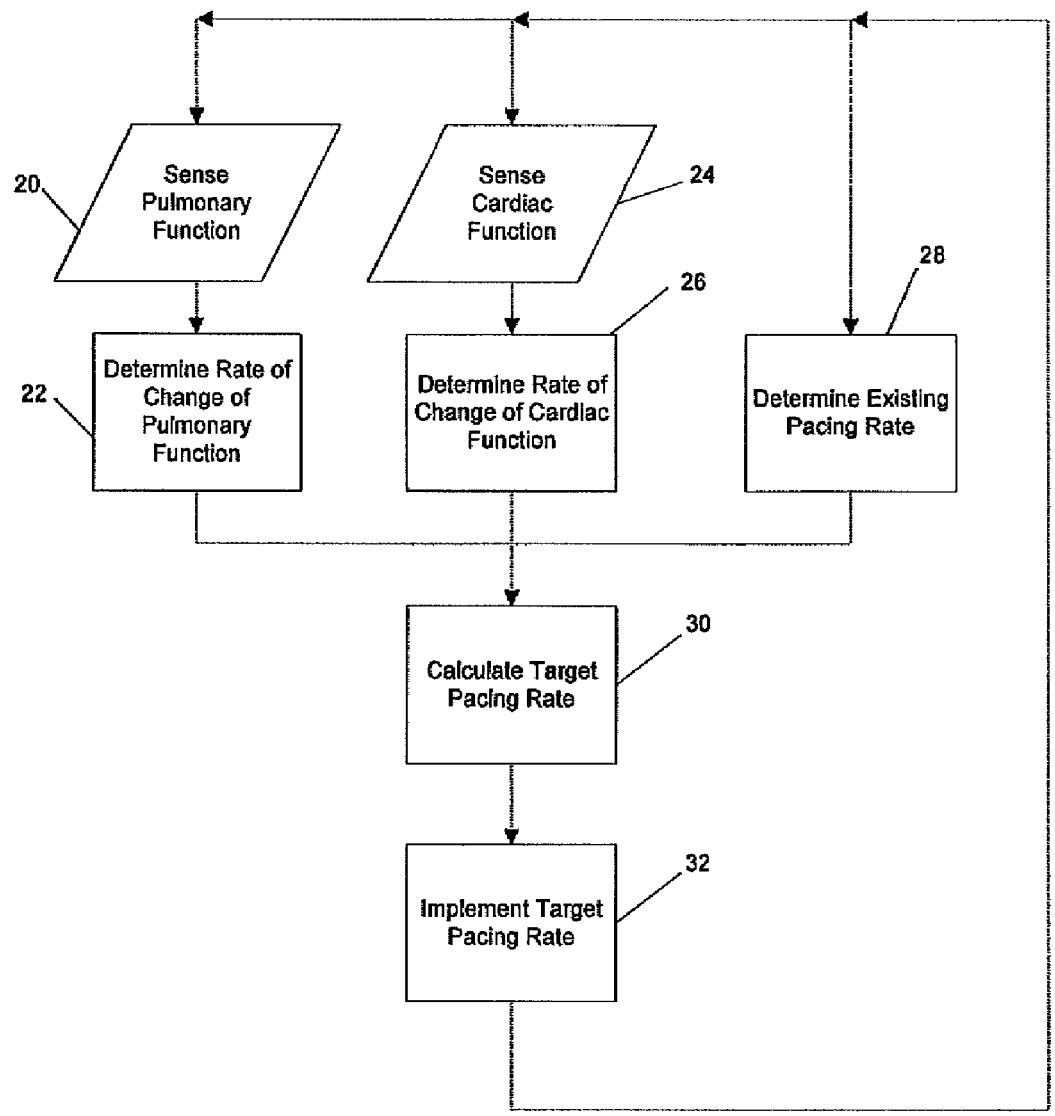
FIG. 3 is a flow chart showing a method for providing rate adaptive pacing according to an embodiment of the present invention.

FIG. 3 is a flow chart of an exemplary method for providing rate adaptive pacing therapy according to an embodiment of the invention. A medical device can include at least one sensor, such that the device is capable of sensing the pulmonary function of the patient and the cardiac function of the patient. The method includes sensing the pulmonary function 20 and determining the rate of change of the pulmonary function 22. Sensing the pulmonary function 20 can take place at a specific point in time or over a period of time. For example, sensing the pulmonary function 20 can take place over time periods spanning seconds, minutes, hours, days, or months. The method also includes sensing the cardiac function 24 and determining the rate of change of the cardiac function 26. Sensing the cardiac function 26 can take place at a specific point in time or over a period of time. For example, sensing the cardiac function 26 can take place over time periods spanning seconds, minutes, hours, days, or months. The device is also capable of determining the existing pacing rate 28, either by sensing the patient's intrinsic pacing rate or by checking the rate at which the device itself is currently delivering pacing pulses to the heart.

The device then calculates a target pacing rate 30 based on the rate of change of the patient's pulmonary function, the rate of change of the patient's cardiac function, and the patient's existing pacing rate. In an embodiment, the target pacing rate is calculated based on the decision matrix shown below in Table 1.

TABLE 1

|  |  | Pulmonary Function | | |
|---|---|---|---|---|
|  |  | ↑ | ↓ | Stable |
| Cardiac Function | ↑ | increase pacing rate | decrease pacing rate | maintain pacing rate |
|  | ↓ | maintain pacing rate | decrease pacing rate | maintain pacing rate |
|  | Stable | increase pacing rate | decrease pacing rate | maintain pacing rate |

As shown in Table 1, if the pulmonary function is decreasing (indicating cessation or reduction of exertion), then in this embodiment the pacing rate is decreased. Specifically, the target pacing rate would be set to a rate lower than the existing pacing rate. If the pulmonary function is increasing (indicating increased exertion), then the target pacing rate would be set to a rate higher than the existing pacing rate so long as the cardiac function is increasing or stable. However, if the pulmonary function is increasing and the cardiac function is decreasing, then further increases in pacing rate would likely lead to inefficient operation of the heart. Therefore, under this condition the target pacing rate is set to the same rate as the existing pacing rate. If the pulmonary function is stable (e.g., not changing with time), then the current pacing rate is maintained (the target pacing rate is set to the same rate as the existing pacing rate).

In some embodiments, when the pulmonary function is increasing or stable and the cardiac function is decreasing, the current pacing rate is maintained temporarily and the cardiac function is reevaluated after a short interval. For example, the cardiac function can be reevaluated after several more beats of the heart. Then if the cardiac function is still decreasing, the pacing rate can be decreased at that time.

It will be appreciated that other decision matrices can be used to aid in setting pacing rates depending on the condition and history of the patient, preferences of the care provider, etc. Table 2 below shows an alternative decision matrix that can be used in an embodiment to calculate a target pacing rate.

TABLE 2

|  |  | Pulmonary Function | | |
|---|---|---|---|---|
|  |  | ↑ | ↓ | Stable |
| Cardiac Function | ↑ | increase pacing rate | decrease pacing rate | maintain pacing rate |
|  | ↓ | decrease pacing rate | decrease pacing rate | decrease pacing rate |
|  | Stable | increase pacing rate | decrease pacing rate | maintain pacing rate |

In contrast to the decision matrix of Table 1, the decision matrix of Table 2 reflects a slightly more conservative pacing strategy. Specifically, in the decision matrix of Table 2, whenever the cardiac function is decreasing with time, the pacing rate is decreased. The decision matrix shown of Table 2 is otherwise the same as the decision matrix of Table 1. This type of pacing strategy can be useful for patients deemed to be at a higher risk of adverse cardiac events such as myocardial infarction. Many other decision matrices can be used depending upon specific therapeutic goals.

After calculating a target pacing rate 30, the device then implements the target pacing rate 32. The device can implement the target pacing rate gradually or may rapidly change the existing pacing rate to match the new target rate. Then the method can be repeated at any desired interval, where each repetition constitutes a pacing evaluation cycle. It will be appreciated that since increases in exertion can occur relatively quickly, the period of time between pacing evaluation cycles should be short enough so that the device can be used to respond to changes in exertion in a timely manner. In some embodiments, the pacing evaluation cycle is repeated at a frequency of greater than about one cycle every hour. In some embodiments, the pacing evaluation cycle is repeated at a frequency of greater than about one cycle every minute. In some embodiments, the pacing evaluation cycle is repeated at a frequency of greater than about one cycle every thirty seconds. In yet other embodiments, the pacing evaluation cycle is repeated at a frequency of greater than about one cycle every five seconds.

Figure 4:
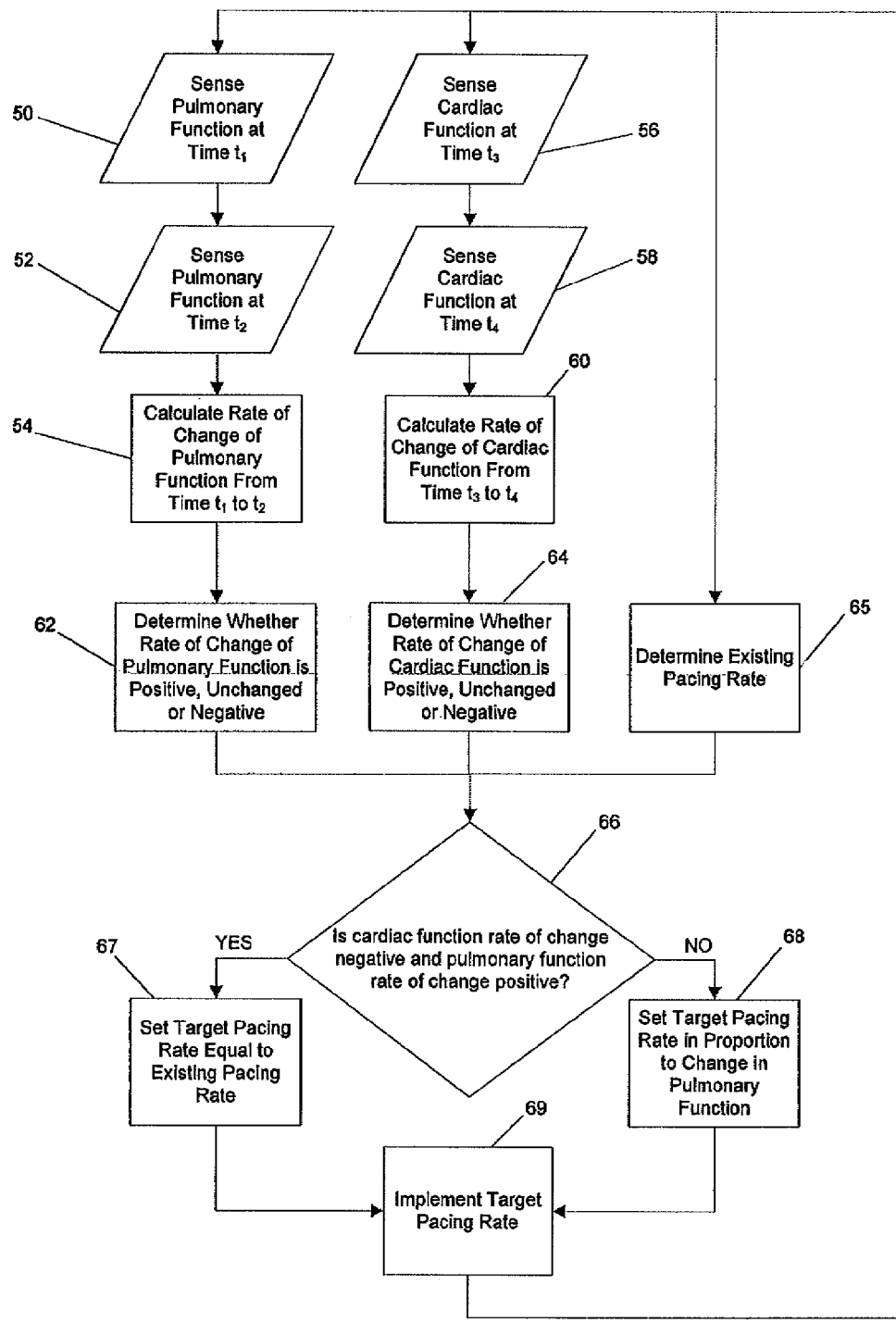
FIG. 4 is a flow chart showing an alternative embodiment of a method for providing rate adaptive pacing.

Another embodiment of a method for providing rate adaptive pacing therapy from a cardiac rhythm management device in response to a patient's exertion is depicted in FIG. 4. This method of providing rate adaptive pacing therapy includes sensing 50 the patient's pulmonary function at a first time $t_1$ and sensing 52 the patient's pulmonary function at a second time $t_2$, and calculating 54 a rate of change of the pulmonary function between time $t_1$ and time $t_2$. The method further includes sensing 56 the patient's cardiac function at time $t_3$ and sensing 58 the patient's cardiac function at time $t_4$, and calculating 60 a rate of change of the cardiac function between time $t_3$ and time $t_4$. In one embodiment, times $t_1$ and $t_3$ are the same and times $t_2$ and $t_4$ are the same. In another embodiment, times $t_1$ and $t_3$ are not the same. In yet another embodiment, the times $t_2$ and $t_4$ are not the same. In another embodiment, the time interval between $t_3$ and $t_4$ is longer than the time interval between $t_1$ and $t_2$. In one embodiment, the time interval between $t_1$ and $t_3$, and/or the time interval between $t_2$ and $t_4$, is greater than about one second and is less than about one minute.

The method includes determining 65 the existing pacing rate, either by sensing the patient's intrinsic pacing rate or by checking the rate at which the device itself is currently delivering pacing pulses to the heart. The method also includes determining 62 whether the rate of change of pulmonary function is positive, unchanged, or negative. The method also includes determining 64 whether the rate of change of cardiac function is positive, unchanged, or negative. Then, the pulmonary and cardiac functions are evaluated 66. If inefficient heart operation is not detected, then the target pacing rate is set 68 in proportion to the change in the pulmonary function. Specifically, unless the cardiac function rate of change is negative while the pulmonary function rate is positive, the method simply adjusts the pacing rate according to how the pulmonary function changes with time. For example, the target pacing rate can be increased when the pulmonary function indicates increasing exertion or the target pacing rate can be decreased when the pulmonary function indicates decreasing exertion. Thus, the method can include setting a desired pacing rate (target pacing rate) by increasing an existing pacing rate proportionately to the rate of change of the pulmonary function when the rate of change of the pulmonary function is positive and the rate of change of cardiac function is not negative. However, if inefficient heart operation is detected, then the target pacing rate is set 67 equal to the existing pacing rate as a precautionary measure. Specifically, if the pulmonary function rate of change is positive but the cardiac function rate of change is negative, then further increases in pacing rate would likely lead to further decreases in efficiency. As such, under those conditions the target pacing rate is set equal to the existing pacing rate. Then the target pacing rate is implemented 69.

In some embodiments of the invention, sensing a pulmonary function can include sensing a parameter that correlates to pulmonary function. Specifically, the parameter can be one correlating to pulmonary function in a manner such that it can be used as an index of exertion. In one embodiment, the parameter that correlates to pulmonary function is respiratory frequency. In another embodiment, the parameter that correlates to pulmonary function is tidal volume. In yet another embodiment, the parameter that correlates to pulmonary function is minute ventilation. In further embodiments, the parameter that correlates to pulmonary function is pulmonary air flow, blood flow, gas arterial and/or pulmonary ($pCO_2$ or $pO_2$) concentrations (air or blood), changes in pulmonary pressure (air or blood), wheezing noises, diaphragmatic movement or myoelectric activity.

It will be appreciated that pulmonary function can be sensed in many different ways. By way of example, pulmonary function can be sensed through changes in pressure, motion, sounds, fluid flow, impedance, etc. Many different sensors capable of sensing pulmonary function are available. The sensor can be an ultrasonic sensor, an optical sensor, a piezoelectric sensor, a strain type sensor, an accelerometer, a magnetic sensor, gas concentration sensor, or the like. In some embodiments, a sensor for detecting pulmonary function is implanted within the patient and a signal corresponding to the pulmonary function is provided to circuitry within the cardiac rhythm management device (such as a pacemaker). The sensor can be within the pulse generator case, on the exterior of the case, disposed along pacemaker leads, or remote from components of the cardiac rhythm management device.

In some embodiments of the invention, sensing a cardiac function can include sensing a parameter that correlates to cardiac function. The parameter can be one correlating to cardiac function in a manner such that it can be used as an index of cardiac efficiency. In one embodiment, the parameter that correlates to cardiac function is a hemodynamic parameter. In one embodiment where the parameter that correlates to cardiac function is a hemodynamic parameter, the hemodynamic parameter is stroke volume. The hemodynamic parameter can also include cardiac output. In another embodiment, the hemodynamic parameter is cardiac contractility. The hemodynamic parameter can also include heart sounds, which can provide an estimation of cardiac contractility and synergy of contraction.

It will be appreciated that cardiac function can be sensed in many different ways. By way of example, cardiac function can be sensed through changes in pressure, motion, strain, stretch, contractility, sounds (valvular or other), vascular and/or ventricular radius, fluid flow, impedance, or any derivative or calculated variable from one of the listed parameters, coronary artery or venous flow, coronary metabolism (lactic acid, $pO_2$, $pCO_2$ or other matabolites), etc. Many different sensors capable of sensing cardiac function are available. The sensor can be a hemodynamic sensor. In some embodiments, the sensor is a hemodynamic sensor that can detect a respiratory artifact. The sensor can be an ultrasonic sensor, an optical sensor, a piezoelectric sensor, a strain type sensor, an accelerometer, a magnetic sensor, or the like. In some embodiments, a sensor for detecting cardiac function is implanted within the patient and a signal corresponding to the cardiac function is provided to circuitry within the cardiac rhythm management device (such as a pacemaker). The sensor can be within the pulse generator case, on the exterior of the case, disposed along pacemaker leads, or remote from components of the cardiac rhythm management device.

By way of example, both pulmonary function and cardiac function can be sensed by detecting the change in the curvature of an optical conductor, such as an optical fiber. The optical fiber can be configured so that bending of the fiber results in changing the optical absorption of the fiber. The optical fiber can be disposed adjacent to the heart or within the heart so that mechanical deformation of the heart (such as during ventricular contraction) can be measured by monitoring the optical absorption of the fiber. Intra-thoracic pressure changes occurring during inspiration and expiration can also affect the bending of the optical fiber and thus pulmonary function can also be measured by monitoring optical absorption of the fiber.

Figure 5:
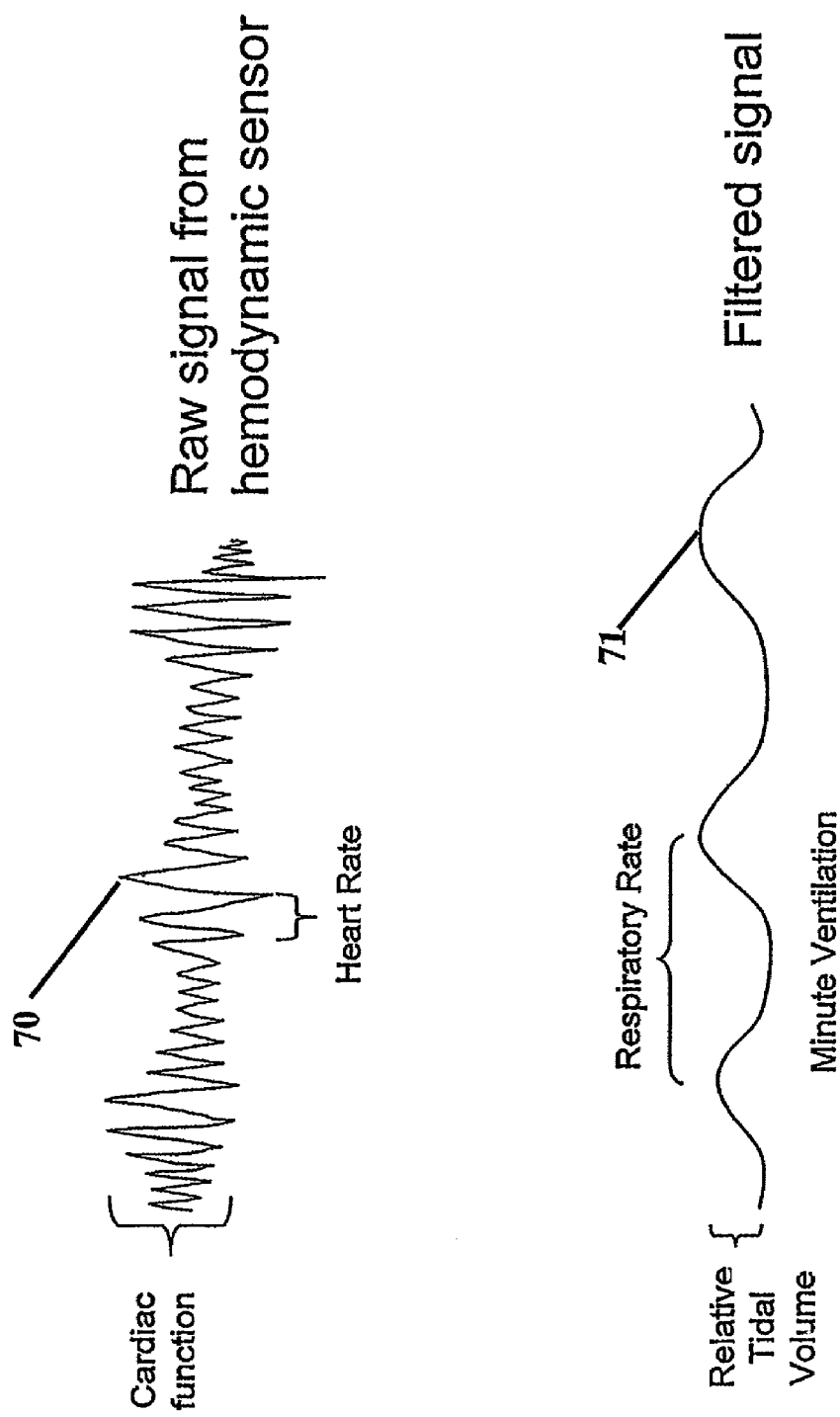
FIG. 5 is a chart showing an idealized raw signal from a hemodynamic sensor and the associated cardiac parameters that can be determined therefrom, and showing a filtered signal with the associated pulmonary parameters that can be determined therefrom.

In some embodiments, separate sensors are used to sense pulmonary function and cardiac function. However, in other embodiments, a single sensor can be used to sense both pulmonary function and cardiac function. Frequently, the raw signal of this sensor initially appears as a changing sinusoidal wave with varying amplitudes corresponding to respiration. FIG. 5 depicts idealized raw sensor data and filtered sensor data that can be obtained from a single sensor, such as an optical fiber based sensor. As is shown in FIG. 5, the heart rate can be determined from sensor signal 70 by measuring the time from signal peak to peak (or from valley to valley, or any other set signal level). The cardiac function, correlating to the cardiac output or stroke volume, can be determined from the magnitude of the signal between any two peaks or valleys or from the slew rate of the signal as measured from peak to adjacent peak or valley to adjacent valley.

Changes in thoracic pressure in the chest can cause the heart to shift position or affect pressures slightly during inspiration and expiration causing a change in hemodynamic parameters. As such, the sensor signal 70 tends to include an artifact that is derived from the changes in thoracic pressure that result from the patient inhaling and exhaling. Thus, the signal 70 can also be processed (i.e., filtered), to produce a filtered signal 71 in order to determine pulmonary function. For example, in the case of an optical conductor positioned within a patient's heart, the sensor signal 70 also tends to include an artifact that is derived from the changes in thoracic pressure that result from the patient inhaling and exhaling. As shown in FIG. 5, the peaks of sensor signal 70 are repeating, where relatively larger peaks tend to occur during expiration, when thoracic pressure is lower, and relatively smaller peaks tend to occur during inspiration, when thoracic pressure is higher. Sensor signal 70 can be processed, where the time between one or more relatively large peaks and the next occurrence of one or more relatively large peaks represents the respiratory rate. The magnitude of the difference between the relatively large peaks and the relatively small peaks correlates to relative tidal volume. Based, then, on the measured respiratory rate and relative tidal volume, a parameter that correlates to minute ventilation can be determined.

Many clinicians calculate a maximum safe heart rate for a patient according to the following formula:

$$R_{MAX}=220-(\text{patient's age})$$

Figure 6:
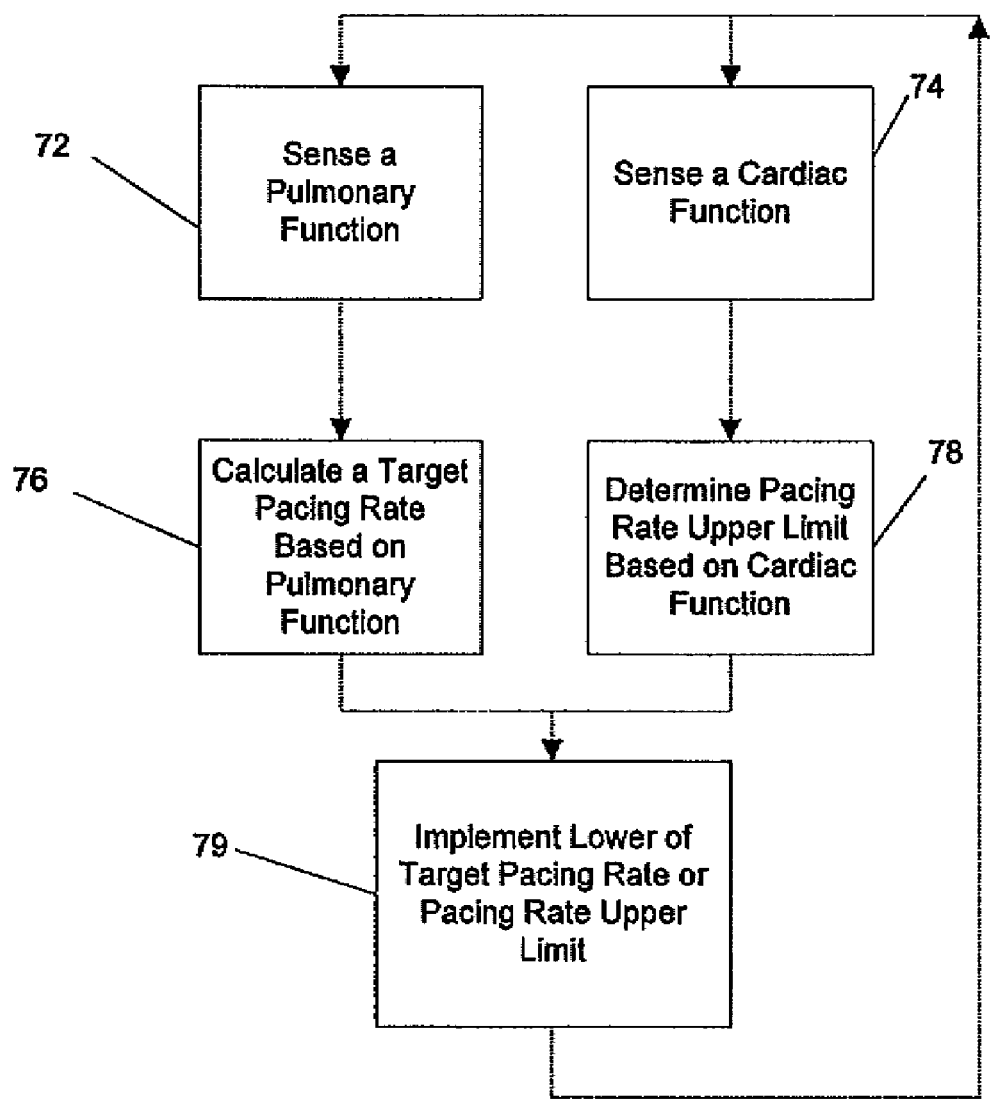
FIG. 6 is a flow chart showing a further alternative embodiment of a method for providing rate adaptive pacing.

In some approaches to delivering pacing therapy, a maximum pacing rate is established according to the same formula. However, because this approach only considers the patient's age, it fails to account for other factors such as individual differences and the progression of disease states. In some embodiments, the invention can include determining a maximum pacing rate (or upper limit) based on sensing a cardiac function. The method depicted in FIG. 6 provides for a method of delivering cardiac pacing therapy to a patient including sensing 72 a pulmonary function and sensing 74 a cardiac function of the patient. Next, the method includes calculating 76 a cardiac pacing rate based on the pulmonary function and calculating 78 a cardiac pacing upper limit based on the cardiac function. The next step is providing 79 cardiac pacing at the calculated cardiac pacing rate so long as the calculated cardiac pacing rate is equal to or less than the cardiac pacing upper limit.

In some embodiments, the cardiac pacing upper limit is derived by determining the point at which the rate of change of the cardiac function becomes negative based on an increased pacing rate. For example, in patients with certain types of cardiac dysfunction, it would be expected that at some point of increasing exertion that the stroke volume plot would naturally have a negative slope. The point at which the cardiac function becomes negative can be determined for these patients each time anew, and/or can be based upon data that is gathered over a period of time (historical data). For example, the maximum pacing rate can be determined based on: 1) new cardiac function data that is being gathered in real time, 2) historical cardiac function data previously gathered for the particular patient, or 3) a combination of real time and historical cardiac function data. The historical cardiac function data can represent and be gathered over any time period desirable. By way of example, the historical cardiac function data can reflect a time period of hours, days, weeks, or months.

Figure 7:
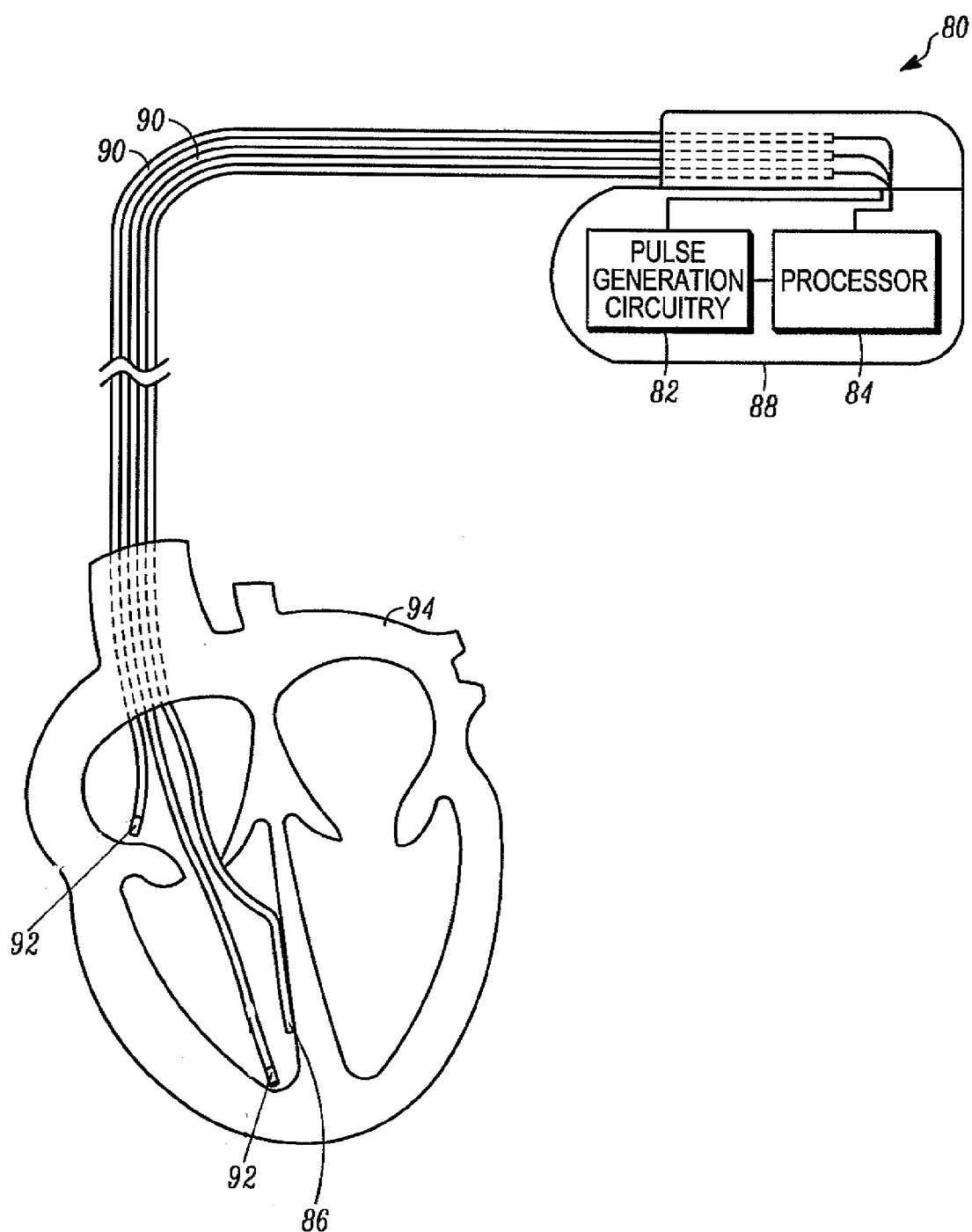
FIG. 7 is a schematic diagram of a cardiac rhythm management device in accordance with an embodiment of the present invention.

Another aspect of the invention relates to a cardiac rhythm management device including rate adaptive pacing features as described herein. A schematic view of a cardiac rhythm management device 80 is shown in FIG. 7. In various embodiments, the cardiac rhythm management device 80 can be a pacemaker, a cardiac resynchronization therapy (CRT) device, a remodeling control therapy (RCT) device, a cardioverter/defibrillator, or a pacemaker-cardioverter/defibrillator. The cardiac rhythm management device 80 includes pulse generation circuitry 82 for generating electrical pulses to be delivered to a heart 94 at a pacing rate. The device 80 also includes a processor 84 in communication with the pulse generation circuitry 82 and one or more sensors 86 for sensing pulmonary function and cardiac function. The one or more sensors 86 are in communication with the processor 84, and the one or more sensors 86 are configured to sense pulmonary function and/or cardiac function. The device can also include a housing or can 88 that contains at least the pulse generation circuitry 82 and the processor 84 and is configured to be implanted within a patient's body. The sensor or sensors 86 may or may not be located within can 88. The sensor or sensors 86 can be positioned to be able to accurately detect cardiac and/or pulmonary function. One or more leads 90 are also provided for transmitting the electrical pulses generated by the pulse generation circuitry 82 to the patient's heart tissue through one or more electrodes 92, where the one or more electrodes 92 are in contact with the patient's heart tissue. In some embodiments, the sensor or sensors 86 are attached to the leads 90. In other embodiments, the sensor or sensors 86 are separate from the leads 90. Processor 84 can be configured to adjust the pacing rate based on the pulmonary function and cardiac function as described herein.

In one embodiment of a cardiac rhythm management device 80, the one or more sensors 86 are a single sensor that is capable of sensing both pulmonary function and cardiac function. In another embodiment, the one or more sensors 86 include a first sensor for sensing pulmonary function and a second sensor for sensing cardiac function. In yet another embodiment, the one or more sensors 86 are configured to detect a change in the curvature of an optical conductor. Alternatively, the one or more sensors 86 can be configured to detect pressure. In a further embodiment, the one or more sensors 86 can be configured to detect a flow rate of a fluid. Yet another embodiment includes the one or more sensors 86 being configured to detect impedance of body tissue.

It will be appreciated that the cardiac rhythm management device 80 can also include other features associated with cardiac rhythm management devices. For example, the cardiac rhythm management device 80 can include features described in commonly assigned U.S. Pat. No. 6,928,325, issued Aug. 9, 2005, the contents of which are herein incorporated by reference.

Another embodiment of the invention relates to a method of adjusting an AV (atrio-ventricular) delay during dual-chamber cardiac pacing therapy. The AV delay refers to the normal delay between the right or left atrium contracting and the corresponding right or left ventricle contracting. This delay permits blood to pass from the atrium into the ventricle before the ventricle begins to contract. In dual chamber cardiac pacing therapy, the AV delay is controllable by the pacing device. However, the appropriate AV delay can vary significantly from patient to patient, particularly given the fact that the population of patients indicated for such pacing therapy will generally have some type of cardiac disease. In addition, an appropriate AV delay for a given individual will change with exertion. If the AV delay is inappropriate, the cardiac stroke volume may decrease, tending to make the heart less efficient at pumping blood. As discussed above, inefficient functioning of the heart can expose the patient to dangers such as ischemia and myocardial infarction as a result of the increased metabolic demands of the cardiac muscle.

Figure 8:
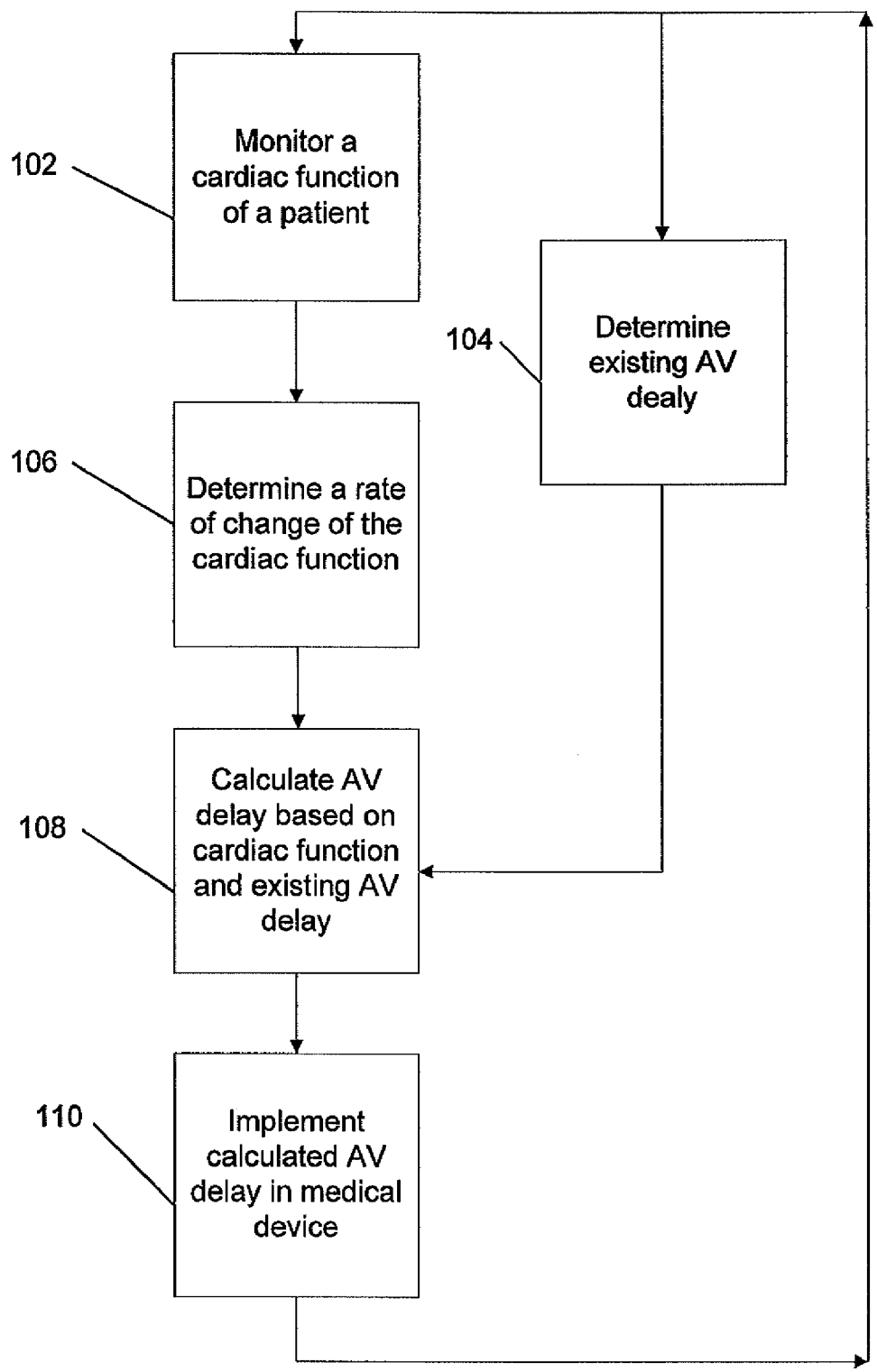
FIG. 8 is a flow chart showing an embodiment of a method for adjusting the atrioventricular (AV) delay during dual-chamber rate-adaptive cardiac pacing therapy While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

For these reasons, it can be desirable to sense a cardiac function, such as stroke volume, in order to determine the appropriate AV delay. Where measurements of cardiac function indicate that cardiac function is decreasing, this provides an indication that the current AV delay may be inappropriate. An embodiment of a method for adjusting an AV delay during dual chamber rate adaptive cardiac pacing therapy is depicted in FIG. 8. The method includes a step 102 of monitoring a cardiac function of a patient, where the cardiac function correlates to a parameter such as stroke volume or cardiac contractility. The method also includes a step 104 of determining or sensing an existing AV delay. The method further includes a step 106 of determining a rate of change in the cardiac function, and a step 108 of calculating a target AV delay based on an existing AV delay and the rate of change in the cardiac function. Finally, the calculated target AV delay is implemented by a medical device, such as a pacemaker, in step 110. The method can then be repeated at any desired interval.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. A method for providing rate-adaptive cardiac pacing therapy from an implantable medical device, the method comprising:
   sensing a pulmonary function of a patient;
   determining a rate of change in the pulmonary function;
   sensing a cardiac function of the patient;
   determining a rate of change in the cardiac function; and
   calculating a target pacing rate based on an existing pacing rate, the rate of change in the pulmonary function, and the rate of change in the cardiac function, wherein calculating the target pacing rate comprises making the target pacing rate less than the existing pacing rate at all times when the pulmonary function is increasing with time and the cardiac function is decreasing with time.

2. The method of claim 1, wherein sensing the pulmonary function comprises sensing a parameter that correlates to pulmonary function, the parameter selected from the group consisting of respiratory frequency, tidal volume, and minute ventilation.

3. The method of claim 1, wherein sensing the cardiac function comprises sensing a parameter that correlates to the cardiac function.

4. The method of claim 3, the parameter that correlates to the cardiac function comprising a hemodynamic parameter.

5. The method of claim 4, the hemodynamic parameter selected from the group consisting of stroke volume, cardiac output, heart sounds, and cardiac contractility.

6. The method of claim 1, further comprising delivering cardiac pacing therapy at the target pacing rate.

7. The method of claim 1, wherein calculating the target pacing rate comprises making the target pacing rate faster than the existing pacing rate when the pulmonary function is increasing with time and the cardiac function is increasing with time.

8. The method of claim 1, wherein calculating the target pacing rate comprises making the target pacing rate less than the existing pacing rate when the pulmonary function is decreasing with time.

9. The method of claim 1, wherein sensing the pulmonary function and sensing the cardiac function are both performed by a single sensor.

10. The method of claim 1, wherein the steps of sensing the pulmonary function and sensing the cardiac function are performed by separate sensors.

11. The method of claim 1, wherein sensing pulmonary function and/or sensing cardiac function comprise sensing a change in the curvature of an optical conductor.

12. The method of claim 1, wherein sensing pulmonary function and/or sensing cardiac function comprise sensing a change in pressure.

13. The method of claim 1, wherein sensing pulmonary function and/or sensing cardiac function comprise sensing a flow rate of a fluid.

14. The method of claim 1, wherein sensing pulmonary function and/or sensing cardiac function comprise sensing impedance across a tissue of the patient.

* * * * *